United States Patent [19]

Tipple

[11] 4,010,761
[45] Mar. 8, 1977

[54] DELIVERY MEANS FOR USE IN VOLUME-CONTROLLED RESPIRATION APPARATUS

[75] Inventor: Neil A. Tipple, Redondo Beach, Calif.

[73] Assignee: Puritan-Bennett Corporation, Santa Monica, Calif.

[22] Filed: Nov. 10, 1975

[21] Appl. No.: 630,083

[52] U.S. Cl. .................................. 128/145.6
[51] Int. Cl.² ................................ A61M 16/00
[58] Field of Search ............... 128/145.5–145.8, 128/142.3; 91/47 R; 92/98 R, 98 D

[56] References Cited

UNITED STATES PATENTS

| | | | |
|---|---|---|---|
| 1,780,336 | 11/1930 | Canton | 91/47 |
| 2,702,023 | 2/1955 | Seehoff | 92/98 D |
| 3,156,238 | 11/1964 | Bird et al. | 128/145.5 |
| 3,859,996 | 1/1975 | Mizzy et al. | 128/173 H |

Primary Examiner—Robert W. Michell
Assistant Examiner—Henry J. Recla
Attorney, Agent, or Firm—Fulwider, Patton, Rieber, Lee & Utecht

[57] ABSTRACT

An improved respirator gas delivery means of the type having a pneumatically-actuated piston slidably mounted in a cylinder, and separated therefrom by a resilient seal, such as a rolling seal or a bellows. An initial flow of air used to actuate the piston is established prior to delivery of a desired volume of breathable gas to a patient. The piston has a valve seal attached to its lower side, cooperating with a valve seat at an exit port in the cylinder, and tending to close the exit port under the weight of the piston. The initial flow of actuating air supports the piston at an equilibrium position allowing the flow to escape through exit port, and prestressing the resilient seal to minimize errors in the delivered volume. Closure of an external exit port valve halts the exit of actuating air, and allows the piston to move upwardly immediately in response to the continued admission of actuating air. Alternative embodiments are disclosed in which the initial flow of actuating air is either a relatively small bleed flow, or the full actuating flow.

13 Claims, 5 Drawing Figures

DELIVERY MEANS FOR USE IN VOLUME-CONTROLLED RESPIRATION APPARATUS

BACKGROUND OF THE INVENTION

This invention relates generally to respiration systems, and, more particularly, to respiration systems in which a preselected volume of air or other breathable gas mixture is delivered to a patient during each breathing cycle.

Typically, the gas is delivered to the patient from a cylinder which contains a movable piston, and the volume of gas delivered from one end of the cylinder is measured by detecting the displacement of the piston in the cylinder. The piston is usually driven by air under pressure admitted at the opposite end of the cylinder and supplied from a separate pneumatic system. When the desired volume of gas has been delivered from the cylinder, the supply of air from the driving pneumatic system is shut off to terminate piston movement. Before the next inspiration phase of the patient breathing cycle, the piston is permitted to return to its initial position, and a new supply of breathable gas is admitted to the cylinder.

In order to minimize the frictional resistance to movement of the piston in the cylinder, either a bellows construction or a rolling seal is used to seal the piston to the cylinder. A rolling seal is basically a folded cylindrical sleeve of resilient material affixed circumferentially to both the cylinder and the piston, and having sufficient length to allow full movement of the piston in the cylinder.

With both the bellows and rolling seal designs, the flexibility of the sealing members introduces the possibility of significant error in the volume of gas delivered to the patient, since, when pneumatic driving pressure is admitted below the piston, the flexibility of the sealing member will cause some gas to be delivered to the patient before movement of the piston begins. Furthermore, there is always a time lag from the time that driving pneumatic pressure is admitted to the cylinder until the time that the piston begins moving and gas is delivered to the patient. Accordingly, there is a need in the respiration art for a volume-limited delivery means which overcomes the aforementioned problems, and the present invention fulfills this need.

SUMMARY OF THE INVENTION

The present invention resides in an improved cylinder and piston assembly in which a substantially constant flow of driving gas is maintained prior to the initiation of delivery of breathable gas to the patient. Briefly, the apparatus of the invention includes means for admitting an initial flow of driving gas to the cylinder prior to the initiation of piston movement, so that the sealing member between the piston and cylinder is inflated and stretched by the drivng gas prior to the start of delivery of the breathing gas, thereby minimizing or eliminating any volume error. Furthermore, the weight of the piston is supported by the driving gas prior to the start of delivery, thus eliminating the aforementioned time lag.

The apparatus also includes an exit port in said cylinder through which the initial flow of driving gas may excape, a valve seat at said exit port, a valve seal affixed to the piston and cooperating with the valve seat to limit the flow of gas from the exit port and thereby maintain a constant pressure of driving gas in the cylinder, and an exit port valve movable to completely seal the exit port when it is desired to raise the piston and deliver breathable gas to the patient.

The delivery means of the invention also includes the conventional elements of the cylinder, the piston, a resilient sealing means between the piston and cylinder, means for admitting the driving gas, and means for admitting the breathable gas to the cylinder and delivering it to the patient. The apparatus may include a separate means for admitting a bleed flow of driving gas to the cylinder, or, alternatively, the initial driving gas flow may be derived from the principal means for admitting the driving gas.

The invention may be embodied in delivery means employing either rolling seals or bellows designs. In either case, the effect of the initial flow of driving gas will be to maintain a substantially constant pressure under the piston, and to maintain it in a floating relationship with the cylinder. When the exit port valve is closed and a substantial flow of driving gas is admitted, the piston is movable immediately in response to the resultant increase of pressure of the driving gas in the cylinder. Moreover, because of the initial pressure of driving gas in the cylinder prior to delivery of the breathable gas, volume errors due to the resilience of the sealing means used are reduced to a minimum.

As previously mentioned, after delivery of a preselected volume of breathable gas to the patient, the piston is allowed to fall to its starting position, and the initial flow of driving gas is resumed, thereby floating the piston again in a position of readiness. In some respiration systems, it has been found that the falling piston will bounce upwardly when the valve seal on the piston impacts against the valve seat at the exit port. This bouncing action may continue for a significant period of time, and may not have subsided before the next inspiration phase.

In accordance with another important aspect of the invention, this piston bounce is minimized by the use of a conically tapered snubber element incorporated into the valve seal affixed to the piston. The snubber comprises a first conical section centrally located on the valve seal, and a second conical section adjoining the first and having a sharper angle of taper. As the piston descends, the snubber is inserted into the exit port, but is sized to provide substantial peripheral clearance. The snubber brings the descending piston smoothly to a halt by a controlled two-stage deceleration which gives the required degree of damping without generating excessive pressure pulses in the remainder of the system.

The apparatus of the invention minimizes volume errors due to the resilience of sealing material between the cylinder and piston, and results in a more rapid response in the delivery of breathable gas to the patient.

Other aspects and advantages of the invention will become apparent from the following more detailed description taken in conjunction with the accompanying drawings.

DETAILED DESCRIPTION

Figure 1:
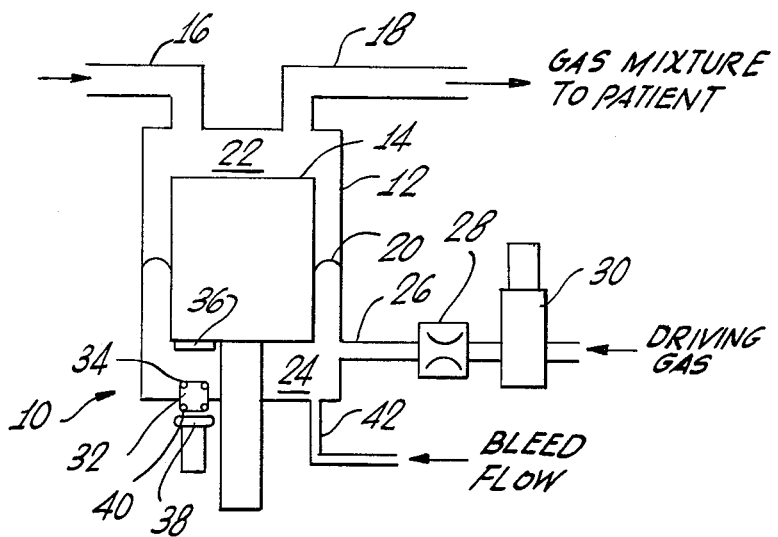
FIG. 1 is a diagrammatic view of a gas delivery means employing the apparatus of one embodiment of the invention in which a bleed flow of driving gas is utilized.

As shown in the drawings for purposes of illustration, the present invention is concerned with a volume-limited delivery means 10 for the delivery of a preselected volume of breathable gas mixture to a critically ill patient, as part of a life support system, or to a patient receiving periodic respiration therapy treatments. In volume-limited respiration systems, a preselected volume of air or other breathable gas mixture is delivered to the patient during the respiration phase of each breathing cycle of the patient. Typically, and as shown in the drawings, the preselected volume is measured by means of a cylinder 12 and a piston 14 movable axially within the cylinder. The breathable gas mixture to be delivered to the patient is admitted to the cylinder 12 on one side of the piston 14, the upper side as illustrated in the drawings. As shown, the breathable gas is admitted to the cylinder 12 through a line 16, and is ultimately delivered to the patient through another line 18. It will be appreciated that, in the diagrammatic view of FIG. 1, various necessary valves, such as a check valve in line 16 to prevent backflow to the supply of breathable gas, have been omitted for clarity.

Some form of low friction sealing means is used between the piston 14 and cylinder 12, typically, as shown in FIGS. 1-4, a rolling seal 20. The rolling seal 20 is essentially a folded, nearly cylindrical sleeve of resilient, usually elastomeric material, slightly tapered from one end to the other. The seal 20 is circumferentially affixed by its ends to both the piston 14 and the cylinder 12, and has sufficient length to allow free movement of the piston over its full displacement.

The rolling seal 20 and the piston 14 effectively divide the cylinder 12 into two chambers, an upper chamber 22 used to contain the gas mixture to be delivered to the patient, and a lower chamber 24, into which a flow of driving gas, usually air, is admitted through a line 26, under the control of a flow-control valve 28 and a solenoid valve 30. When it is desired to deliver the preselected volume of gas to the patient, driving gas is admitted into the lower chamber 24, and the piston 14 is thereby raised to deliver the gas to the patient from the upper chamber 22. After delivery of the gas to the patient, the lower chamber 24 is vented, the piston 14 is allowed to fall to its starting position, and the upper chamber 22 is again filled with the breathable gas mixture, supplied through the line 16.

The basic volume-limited gas delivery system as described thusfar suffers from a significant volume error due to the resilience of the rolling seal 20, and there is an inherent time lag between the time of admission of the driving gas and the beginning of delivery of gas to the patient, as driving gas pressure builds up in the lower chamber 24.

In accordance with the present invention, a flow of driving gas into the chamber 24 is established and maintained before it is desired to start delivering gas to the patient. The apparatus of the invention includes an exit port 32 in the cylinder 12, connecting with the lower chamber 24, a valve seat 34 affixed to the exit port, and a valve seal 36 affixed to the bottom of the piston 14 and located to cooperate with the valve seat 34. Also included is an exit port valve 38 positioned to cooperate with another valve seat 40 located at the outer end of the exit port 32.

In the embodiment shown in FIG. 1, the initial flow of driving gas, i.e., prior to the movement of the piston 14 to deliver gas to the patient, is provided through a separate bleed-flow line 42 into the lower chamber 24. Prior to the delivery of gas to the patient, the exit port valve 38 will be open, and the bleed-flow supplied through line 42 will exit through the exit port 32. However, the weight of the piston 14 will tend to keep the valve seal 36 seated on the valve seat 34, and thus block the exit port 32. As the pressure in the lower chamber 24 builds up because of the incoming bleed flow on line 42, the piston 14 is raised slightly to allow an exit flow around the seal 36 and through the exit port 32. An equilibrium point is reached at which the cylinder 14 is raised just sufficiently to permit an exit flow equal to the input bleed flow, and to maintain a substantially constant pressure in the chamber 24.

When it is desired to begin delivery of gas from the upper chamber 22 to the patient, a full flow of driving gas is admitted to the lower chamber 24 by opening the solenoid valve 30, and simultaneously closing the exit port valve 38 to seal the lower chamber 24. Since the piston 14 was previously in a state of equilibrium, delivery of gas from the upper chamber 22 will begin almost instantaneously on the admission of the full flow of driving gas to the lower chamber 24. Furthermore, volume errors due to the resilience of the rolling seal 20 are practically eliminated, since the pressure in the lower chamber 24 due to the bleed-flow also serves to maintain the rolling seal in a prestressed condition prior to delivery of the breathable gas.

Figure 2:
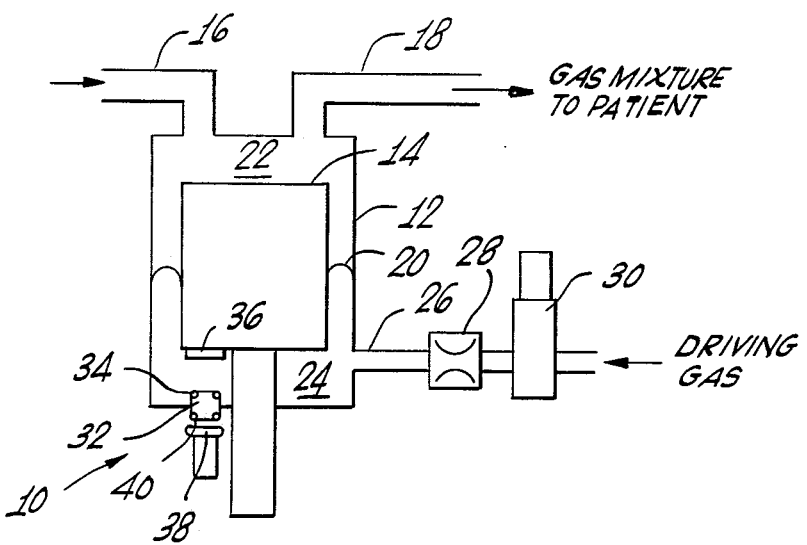
FIG. 2 is a diagrammatic view similar to FIG. 1 but showing an alternative embodiment of the invention in which the full flow of driving gas is utilized.

The embodiment illustrated in FIG. 2 is similar to that shown in FIG. 1 except in one important respect. Full flow, rather than bleed flow, of the driving gas into the lower chamber 24 is utilized to float the piston 14 to its equilibrium position, and to inflate and stress the rolling seal 20. It will be appreciated that the full flow of driving gas will, in most respiration systems, be adjustable according to patient requirements. Accordingly, the piston 14 will not always float at the same axial position prior to the delivery of gas to the patient from the upper chamber 22. Clearly, this factor introduces an error into the determination of the volume of gas delivered to the patient, since the starting position of the piston 14 is variable, and is dependent upon the value of the full flow of the driving gas through the line 26. However, this variable starting position of the piston 14 can be easily compensated for by means of conventional electrical measurement techniques.

Delivery of gas to the patient is initiated in the FIG. 2 embodiment by closing the exit port valve 38. As in the FIG. 1 embodiment, the resultant increase in pressure in the lower chamber 24 immediately causes delivery of gas from the upper chamber 22, and the delivery response is extremely rapid. It will also be apparent that the FIG. 2 embodiment has another advantage in that the full flow of driving gas is maintained uniformly at all times. This tends to eliminate pressure transients in the system, and provides for much smoother operation of the system.

Figure 3:
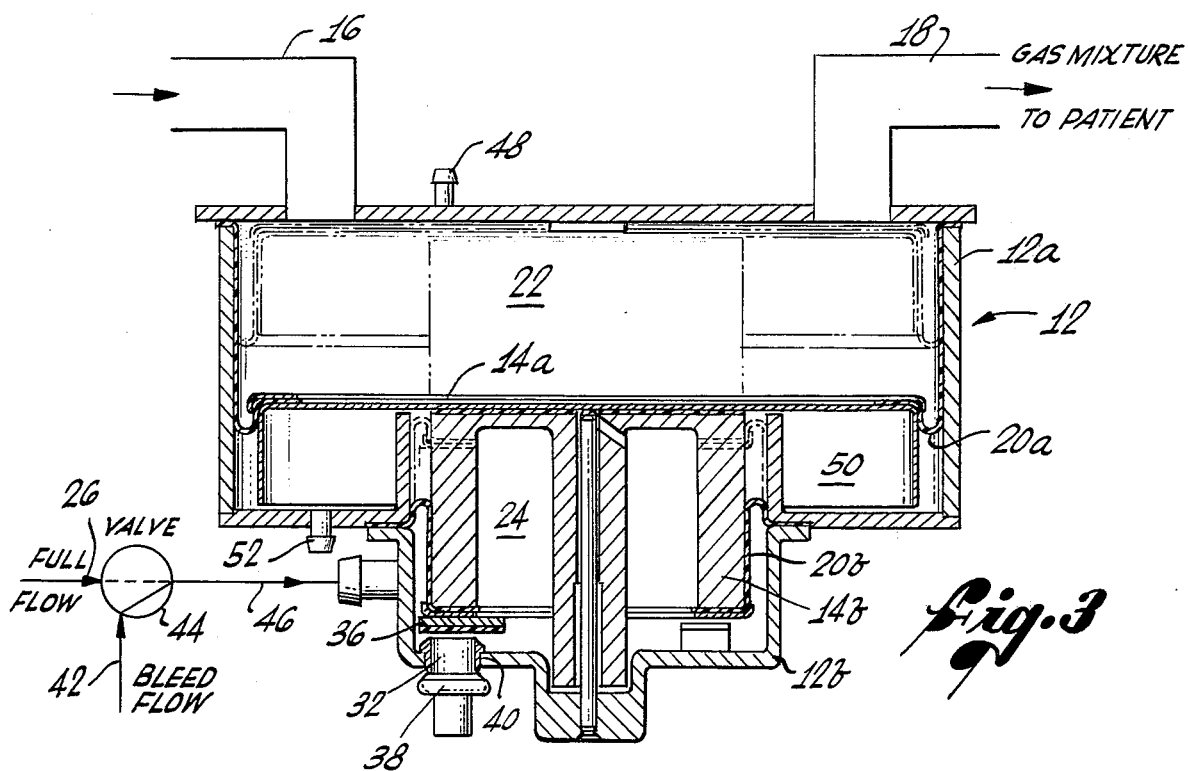
FIG. 3 is a more detailed sectional view of a piston and cylinder assembly utilizing the invention.

FIG. 3 is a more detailed sectional view of a cylinder 12 and piston 14 embodying the invention in accordance with the bleed-flow principal described in connection with FIG. 1. In this particular form of the invention, the bleed-flow line 42 and the full-flow line 26 are routed through a two-position valve 44, by means of which either the bleed flow or the full flow may be selected for communication with the lower chamber 24 through line 46. The connection shown at 48 is provided to allow pressure measurement in the upper chamber 22. The rolling seal 20 of FIG. 1 is modified in the FIG. 3 embodiment, to the extent that two rolling seals 20a and 20b are used. The cylinder 12 has an upper portion 12a, and a lower portion 12b of substantially smaller diameter than the upper portion, and the piston 14 similarly has an upper portion 14a comparable in size to the upper portion 12a of the cylinder, and a lower portion 14b comparable in size with the lower portion 12b of the cylinder.

The first rolling seal 20a is positioned between the upper portions 12a and 14a of the cylinder and piston, and the lower rolling seal 20b is similarly positioned between the lower portions 12b and 14b of the cylinder and piston. It can be seen that this construction creates an intermediate chamber 50 between the two rolling seals 20a and 20b. This intermediate chamber 50 is connected by a passage 52 to atmospheric, or lower than atmospheric pressure, and this relatively low pressure therefore acts to keep the rolling seals 20a and 20b inflated toward the intermediate chamber at all times. The exit port valve 38 is of a conventional pneumatic type having an inflatable element which is compressed by inflation against the seat 40.

Figure 4:
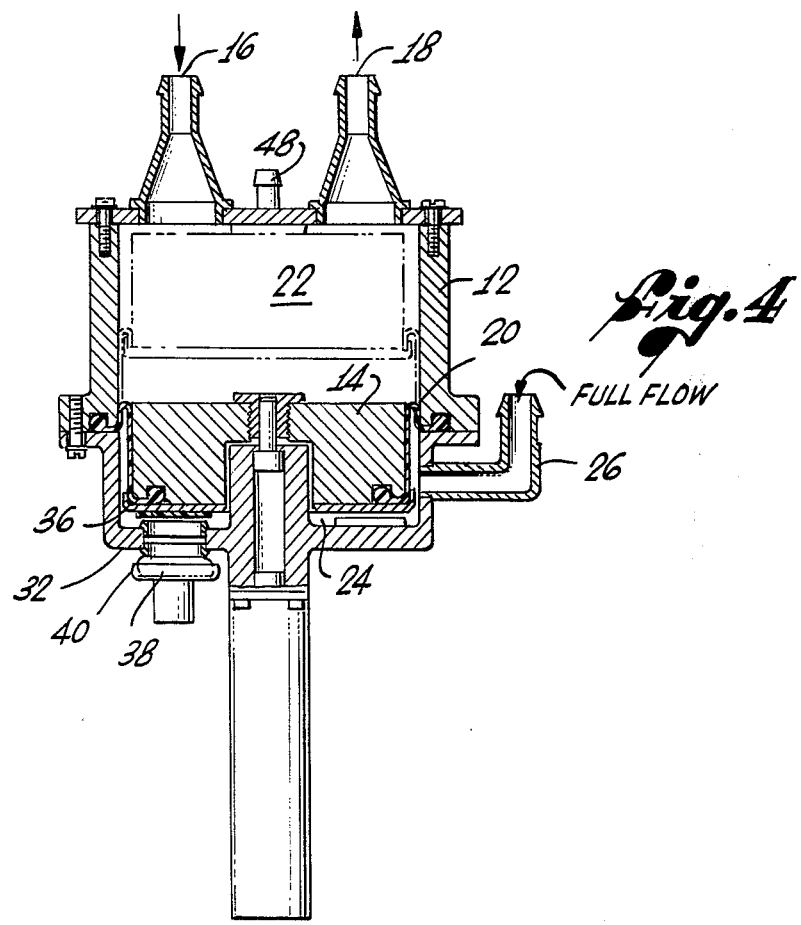
FIG. 4 is a sectional view of another form of piston and cylinder assembly utilizing the invention.

FIG. 4 is a detailed sectional view of the full-flow embodiment illustrated diagramatically in FIG. 2. Again, the connection shown at 48 is for pressure measurement in the upper chamber 22 of the cylinder 12. In this version, only a single rolling seal 20 is employed.

As mentioned earlier, when the preselected volume of gas has been delivered to the patient, the piston 14 is allowed to fall to its starting position, the exit port valve 38 is opened, and a flow of gas is admitted to the lower chamber 24 to re-establish an equilibrium position for the piston. For some designs of the piston 14, the descending piston may bounce when the seal 36 impacts against the seat 34, and the bouncing may continue for a short period of time until equilibrium is again reached. Unfortunately, in some designs, this bouncing may continue until it is time to deliver another volume of gas to the patient from the cylinder 12.

Figure 5:
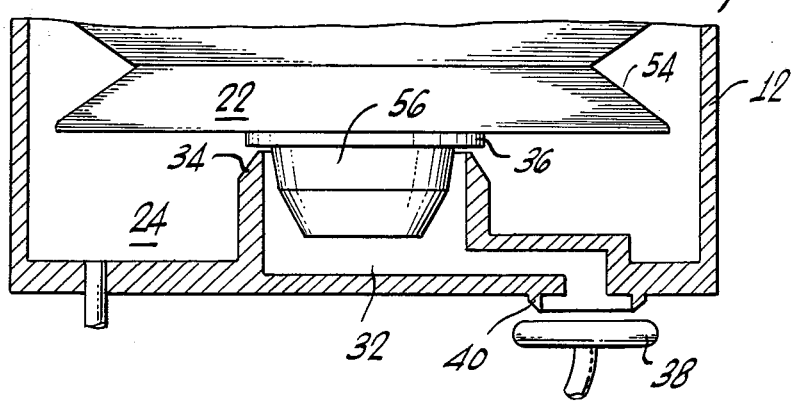
FIG. 5 is a fragmentary view, shown partly in section, showing an improved valve seating arrangement which may be utilized in the invention apparatus.

The modification illustrated in FIG. 5 has been found to be useful in damping out these bouncing vibrations of the piston 14, so that a stable equilibrium condition is reached well before the time of the next patient inspiration phase. FIG. 5 shows a portion of a cylinder 12 and a bellows 54 for delivering the gas to the patient. The lower chamber 24 is formed by the space below and outside the bellows 54 and the upper chamber 22 is formed by the space inside the bellows. The illustrated cylinder 12 has an exit port 32, an exit port valve 38, valve seats 34 and 40, and a valve seal 36, all similar to corresponding elements in the previously described embodiments. In addition, however, affixed to the valve seal 36 is a snubber 56 comprising a generally conically shaped element attached to and depending from the seal.

More specifically, the snubber 56 includes a base frusto-conical section tapered to an angle of approximately 10° with respect to the axis of the cylinder 12, and an adjoining outer or distal frusto-conical section tapered to a steeper angle, approximately 30° in the illustrative embodiment. The snubber 56 is centrally mounted on the seal 36, and, as the seal approaches the seat 34, the snubber enters the opening of the exit port 32 with a substantial clearance. As the distal section of the snubber 56 enters the exit port 32 there is an immediate but gradual increase in the resistance to the downward movement of the bellows 54, because of the increased resistance to the flow of air through the exit port 32. Consequently, the deceleration of the descending bellows 54 is gradually and moderately increased, without sudden shock loads or resultant oscillations. Then, as the base portion of the snubber 56 enters the exit port 32, the smaller angle of taper of that portion provides a slower increase in the deceleration. Ideally, the base portion of the snubber will provide a zero rate of change of deceleration, i.e., a uniform deceleration, and the seal 36 will be smoothly decelerated to its equilibrium position, substantially without any bouncing motion. In effect, the snubber 56 provides a smooth two-stage deceleration of the descent of the bellows 54, and thereby damps out any vibrations resulting from a too rapid descent. It will be appreciated that the snubber 56, while shown installed in apparatus of the bellows type, could be employed equally well in apparatus of the rolling seal type.

It will be appreciated from the foregoing that the present invention has substantially advanced the art of volume-limited respirators. In particular, it provides novel means for minimizing errors in the volume of gas delivered to the patient, and for increasing the speed of response of the volume delivery apparatus. It will also be appreciated that, although particular embodiments of the invention have been described in detail for purposes of illustration, various modifications may be made without departing from the spirit and scope of the invention. Accordingly, the invention is not to be limited, except as by the appended claims.

I claim:

1. Gas delivery apparatus for use with a respirator system, said apparatus comprising:

a cylinder;

a piston slidably mounted in said cylinder;

sealing means affixed to said cylinder and to said piston, effectively dividing said cylinder into first and second chambers, said first chamber having connected thereto an input line for admitting a gas mixture to be delivered to a patient and an output line for delivering a desired volume of the gas mixture to the patient on movement of said piston, and said second chamber having an exit port therein;

means for admitting an initial flow and a subsequent flow of actuating gas into said second chamber;

valve means for venting gas from said second chamber, through said exit port when said initial flow is admitted into said second chamber, including a valve seal attached to said piston and a valve seat located about said exit port and engageable with said valve seal; and means for completely sealing said exit port when said subsequent flow of actuating gas is admitted into said second chamber to displace said piston and drive the desired volume of gas from said first chamber;

whereby the initial flow of actuating gas exits said second chamber through said valve means and said exit port, and establishes a pressure in said second chamber sufficient to hold said piston in an equilibrium position, with said sealing means being prestressed by the pressure in said second chamber, to minimize volume errors, and said piston being movable in rapid response to further increase in the actuating pressure when said exit port is completely sealed by said sealing means.

2. Apparatus as set forth in claim 1, wherein said means for admitting a flow of actuating gas includes:
   means for admitting a uniform bleed flow of actuating gas to establish an initial pressure in said second chamber and to float said piston in an equilibrium position; and
   means separate from said means for admitting a uniform bleed flow of actuating gas, for admitting a full flow of actuating gas when it is desired to displace said piston.

3. Apparatus as set forth in claim 1, wherein said means for admitting a flow of actuating gas admits a full flow of gas to said second chamber at all times, and said piston is displaced by closing said means for sealing said exit port.

4. Apparatus as set forth in claim 1, wherein said sealing means includes a rolling seal affixed to said piston and said cylinder.

5. Apparatus as set forth in claim 1, wherein said sealing means includes a bellows assembly.

6. Apparatus as set forth in claim 1, wherein:
   said exit port includes an upstanding, open-ended, substantially cylindrical portion; and
   said valve means further includes a tapered snubber element mounted on said valve seal and located centrally thereon in order to enter said valve seat and said upstanding portion of said exit port with substantial clearance, to decelerate said piston in its descent after delivering gas from said first chamber, whereby said tapered snubber element provides a graduated increasing resistance to the exit flow of actuating gas, and therefore a graduated increase in pressure in said second chamber as said piston descends.

7. Apparatus as set forth in claim 6, wherein said snubber element includes:
   a distal conical section to provide a first stage of piston deceleration; and
   an adjoining base conical section having a smaller angle of taper than said distal section, to provide a second stage of piston deceleration.

8. Gas delivery apparatus for use with a respirator system, said apparatus comprising:
   a cylinder;
   a piston slidably mounted in said cylinder;
   sealing means between said piston and said cylinder, effectively dividing said cylinder into an upper chamber from which a preselected volume of gas is to be delivered, and a lower chamber into which actuating gas is to be admitted to displace said piston;
   means for admitting an initial flow and a subsequent flow of actuating gas into said lower chamber;
   an input line connected to said upper chamber for delivering a gas mixture thereto;
   an output line connected to said upper chamber for delivering the preselected volume of gas to a patient on upward displacment of said piston;
   an exit port in said lower chamber;
   first exit port sealing means responsive to said initial flow of actuating gas attached to said piston and tending to seal said exit port under the weight of said piston and the pressure of gas in said upper chamber, whereby said initial actuating gas flowing into said lower chamber operates to lift said piston and said first exit port sealing means to a position of equilibrium, thereby maintaining a substantially constant flow through said lower chamber and prestressing said sealing means from below to minimize errors in the volume delivered from said upper chamber; and
   second exit port sealing means responsive to said subsequent flow of actuating gas operable to completely seal said exit port and thereby actuate said piston in rapid response to admission of said subsequent flow of actuating gas into said lower chamber.

9. Apparatus as set forth in claim 8, wherein said means for admitting a flow of actuating gas into said lower chamber includes:
   first means, for admitting a relatively low and uniform bleed flow to pressurize said lower chamber and raise said piston to its equilibrium position; and
   second means for admitting a full flow when it is desired to displace said cylinder.

10. Apparatus as set forth in claim 8, wherein said sealing means is a rolling seal comprising a folded, substantially cylindrical sleeve affixed by its ends to said cylinder and to said piston.

11. Apparatus as set forth in claim 8, wherein said sealing means includes a bellows.

12. Apparatus as set forth in claim 8, wherein:
   said exit port includes an upstanding, openended, substantially cylindrical portion; and
   said first exit port sealing means includes a tapered snubber element located to be inserted in said upstanding portion of said exit port with substantial radial clearance as said piston descends after delivering gas from said upper chamber, whereby said tapered snubber element operates to slow the rate of descent of said piston gradually and to minimize bounce.

13. Apparatus as set forth in claim 12, wherein said snubber element includes:
   a distal conical section to provide a first stage of piston deceleration at a gradually increasing rate; and
   an adjoining base conical section having a smaller angle of taper than said distal section, to provide a second stage of piston deceleration at an approximately uniform rate.

* * * * *

UNITED STATES PATENT AND TRADEMARK OFFICE
CERTIFICATE OF CORRECTION

PATENT NO. : 4,010,761
DATED : March 8, 1977
INVENTOR(S) : Neil A. Tipple

It is certified that error appears in the above-identified patent and that said Letters Patent are hereby corrected as shown below:

Column 1, line 66, "excape" should be --escape--.

Column 8, line 7, "displacment" should be --displacement--;
         line 42, "openended" should be --open ended--.

Signed and Sealed this nineteenth Day of July 1977

[SEAL]

Attest:

RUTH C. MASON
Attesting Officer

C. MARSHALL DANN
Commissioner of Patents and Trademarks